United States Patent
Miyashita

(10) Patent No.: US 8,337,779 B2
(45) Date of Patent: Dec. 25, 2012

(54) REAGENT OPEN MECHANISM OF LUMINESCENCE MEASUREMENT SYSTEM AND OPEN NEEDLE CONTROL METHOD IN REAGENT OPEN MECHANISM

(75) Inventor: Noe Miyashita, Tokyo (JP)

(73) Assignee: Hitachi Plant Technologies, Ltd., Tokyo (JP)

( * ) Notice: Subject to any disclaimer, the term of this patent is extended or adjusted under 35 U.S.C. 154(b) by 122 days.

(21) Appl. No.: 12/974,284

(22) Filed: Dec. 21, 2010

(65) Prior Publication Data

US 2011/0171670 A1  Jul. 14, 2011

(30) Foreign Application Priority Data

Dec. 21, 2009 (JP) ................................. 2009-289736

(51) Int. Cl.
*C12Q 1/66* (2006.01)

(52) U.S. Cl. .......... 422/512; 422/51; 422/501; 422/509; 422/517; 422/518; 422/519; 422/520; 422/524

(58) Field of Classification Search .................. 422/501, 422/51, 517, 518, 520, 509, 512, 519, 524
See application file for complete search history.

(56) References Cited

U.S. PATENT DOCUMENTS

| | | | |
|---|---|---|---|
| 4,577,514 A * | 3/1986 | Bradley et al. | 73/863.01 |
| 4,624,148 A * | 11/1986 | Averette | 73/864.21 |
| 4,721,137 A | 1/1988 | Muller | |
| 4,774,055 A | 9/1988 | Wakatake et al. | |
| 5,935,523 A * | 8/1999 | McCandless et al. | 422/510 |
| 5,945,070 A * | 8/1999 | Kath et al. | 422/535 |
| 2005/0223822 A1 * | 10/2005 | Ozbal | 73/864.41 |
| 2006/0263250 A1 * | 11/2006 | Blouin et al. | 422/63 |
| 2008/0241871 A1 | 10/2008 | Okanojo et al. | |
| 2009/0044607 A1 | 2/2009 | Hochgraeber et al. | |

FOREIGN PATENT DOCUMENTS

| | | |
|---|---|---|
| CA | 2 092 742 | 8/2001 |
| DE | 10 2004 03815 | 2/2006 |
| JP | 5-87568 | 11/1993 |
| JP | 5-509158 | 12/1993 |

(Continued)

OTHER PUBLICATIONS

EP Search Report of Appln. No. 11152616.6 dated Nov. 28, 2011 in English.

(Continued)

*Primary Examiner* — Brian R Gordon
*Assistant Examiner* — Shogo Sasaki
(74) *Attorney, Agent, or Firm* — Antonelli, Terry, Stout & Kraus, LLP.

(57) ABSTRACT

A reagent open mechanism of the luminescence measurement system comprises a triaxial actuator and a reagent dispensing nozzle which is driven by the triaxial actuator. A reagent cartridge where a reagent to be divided by the reagent dispensing nozzle is filled in a concave and the opening of the concave is sealed by an aluminum sheet can be set in. This reagent open mechanism comprises an open needle which is driven by the triaxial actuator and makes a hole in the aluminum sheet and a fixation block between the reagent dispensing nozzle and the open needle which arranges the reagent dispensing nozzle and the open needle in such location that the reagent dispensing nozzle or the open needle does not contact with a structure including the reagent cartridge in a Z-axis operation during opening time or reagent dividing and dispensing time.

6 Claims, 10 Drawing Sheets

FOREIGN PATENT DOCUMENTS

| | | |
|---|---|---|
| JP | 11-155597 | 6/1999 |
| JP | 2000-314738 | 11/2000 |
| JP | 2004-264044 | 9/2004 |
| JP | 2004-313028 | 11/2004 |
| JP | 2005-037179 | 2/2005 |
| JP | 2007-003351 | 1/2007 |
| JP | 2007-014255 | 1/2007 |
| JP | 2007-155646 | 6/2007 |
| JP | 2008-249628 | 10/2008 |
| WO | WO 91/19181 | 12/1991 |

OTHER PUBLICATIONS

JP Search Report of Appln. No. 2009-289736 dated Dec. 14, 2011.
Singapore Search Report dated Jun. 30, 2011 in English.

* cited by examiner

Fig. 3-A
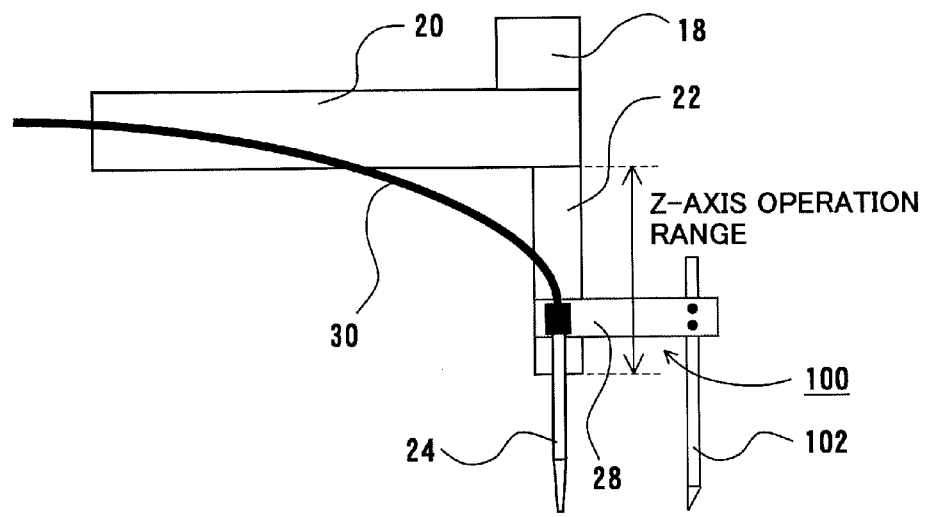
Fig. 3-B
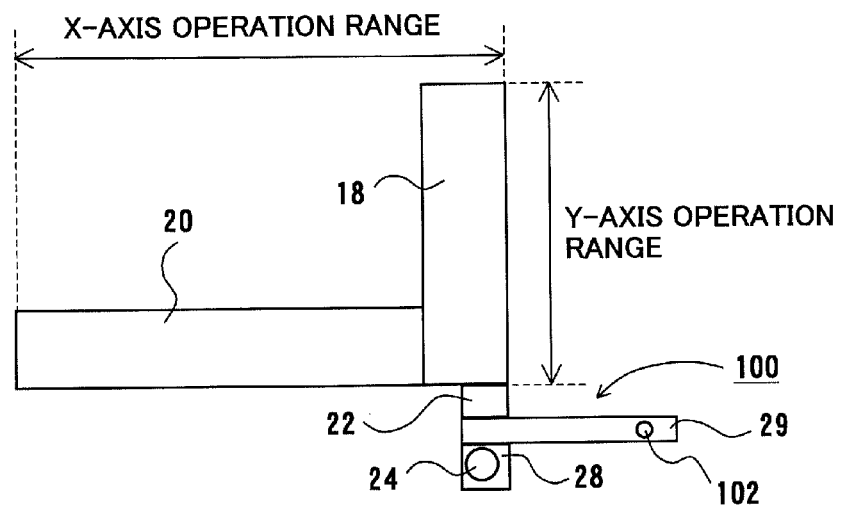

Fig. 5-A
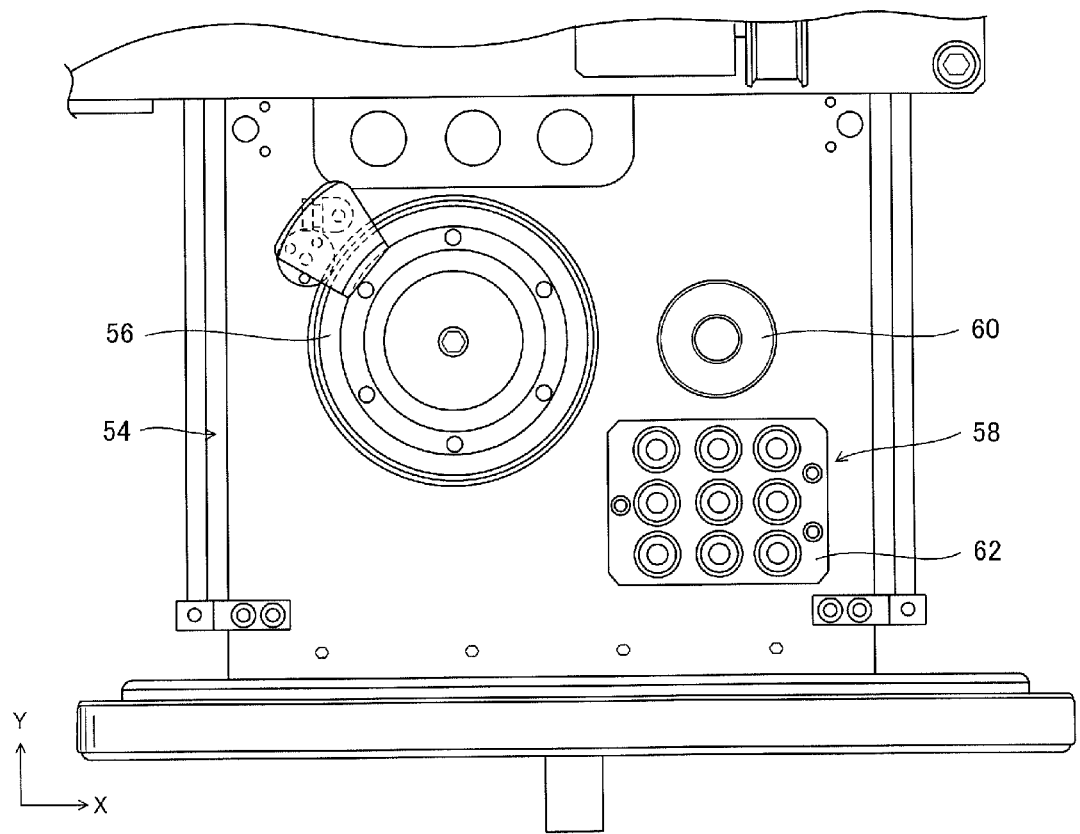
Fig. 5-B
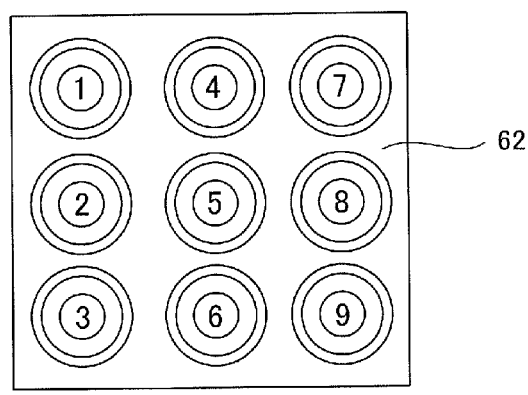

REAGENT OPEN MECHANISM OF LUMINESCENCE MEASUREMENT SYSTEM AND OPEN NEEDLE CONTROL METHOD IN REAGENT OPEN MECHANISM

BACKGROUND (a) Field of the Invention

The present invention relates to a mechanism for automatically opening a reagent pack used in a test by a luminescence measurement system and a method of controlling an open needle in the mechanism.

(b) Description of the Related Art

Asepsis and specific biological cleanliness of work environment are required in various clinical sites, food factories, medicinal product manufacturing factories, sites of fundamental researches, and the like. In such the environment requiring the biological cleanliness, the number of microorganisms in the air (airborne bacteria), falling bacteria, adhesive bacteria, and the like are counted (viable bacteria count). As a method of measuring airborne bacteria, an airborne bacteria sampler for collecting floating bacteria by natural fall of floating bacteria and by suctioning a certain amount of air has been commonly employed.

In these methods, ordinarily, floating bacteria are collected on an agar plate, cultured by a thermostat device for two to three days, and a number of colonies generated after the culture is counted as the number of viable bacteria. However, this method has a problem that it requires long time to culture viable bacteria.

Meanwhile, as a method capable of counting the number of microorganisms in short time, a method of converting the number of microorganisms by measuring ATP (Adenosine TriPhosphate) being an intracellular component by a bioluminescence method is well known.

The bioluminescence method employs a luciferin-luciferase luminescence reaction, where a luminescence reagent which contains basic luciferin and enzyme luciferase is mixed with a sample solution which contains ATP extracted from a cell of microorganism, ATP amount is obtained from a luminescence amount which is produced by the reaction, and the number of viable bacteria is calculated based on ATP amount per one viable bacterium. Patent document 1 discloses a kit for counting the number of viable bacteria by using such the luminescence reaction.

According to a method of counting the number of viable bacteria by a kit disclosed in Japanese Unexamined Patent Application Publication No. H11-155597 (Patent document 1), it is possible to achieve the assured effect in terms of reduction of measurement time. However, in a case where ultra minute amount of viable bacteria is subjected to count, a luminescence amount itself is minute. Therefore, there is a problem of great influence of background luminescence caused by such as inclusion of residual ATP and ATP not to be counted, and it is impossible to obtain good measurement accuracy.

Meanwhile, in a luminescence measurement system disclosed in Japanese Unexamined Patent Application Publication No. 2008-249628 (Patent document 2), viable bacteria adhered to a nozzle for dispensing a reagent and background luminescence derived from residual ATP are controlled, so that luminescence measurement can be conducted accurately and promptly.

According to the luminescence measurement system disclosed in the Patent document 2, it is considered possible to measure accurately and promptly even though minute amount of viable bacteria is luminescence-counted. However, in a case where viable bacteria count in minute amount is possible by the system disclosed in Patent document 2, contamination inside the system exerts great influence on a count value. For example, a reagent used for luminescence measurement is set in the system after it is opened outside the system, there is a possibility of contamination occurred during a period from opening to setting in the system.

SUMMARY

An object of the present invention is to provide a means capable of controlling introduction of viable bacteria to an inside of the system and occurrence of contamination inside the system. Further object is to particularly provide an automatic reagent open mechanism in the luminescence measurement system, and an open needle control method for a reagent open mechanism.

In order to achieve the above objects, a reagent open mechanism of a luminescence measurement system according to the present invention has a configuration described below. A reagent open mechanism of a luminescence measurement system capable of setting a reagent cartridge, where a reagent is filled in a concave and an opening of the concave is sealed by a film, comprising:

a triaxial actuator where horizontal movement is represented by X axis and Y axis and vertical movement is represented by Z axis;

a reagent dispensing nozzle which is driven by the triaxial actuator and capable of dividing a reagent from the reagent cartridge;

an open needle which is driven by the triaxial actuator and makes a hole in the film; and a fixation block between the reagent dispensing nozzle and the open needle which arranges the reagent dispensing nozzle and the open needle in such a location that the reagent dispensing nozzle or the open needle does not contact with component elements of the luminescence measurement system including the reagent cartridge in a Z-axis operation during film opening time or reagent dividing and dispensing time.

Further, in the reagent open mechanism of the luminescence measurement system having the above features, a diameter of the open needle is preferably larger than that of the reagent dispensing nozzle. Such the configuration allows no contact between a film surface after being opened and the reagent dispensing nozzle. Accordingly, it is possible to prevent contamination of the reagent dispensing nozzle through the film surface.

Further, in the reagent open mechanism of a luminescence measurement system having such the features, the open needle is a cylinder with an obliquely-cut tip end, and end face has a portion acute with a side face and a portion obtuse to a side face. According to such the configuration, the film is torn at the acute portion, and it is not torn (cut off) but pressed and bent at the obtuse portion. Therefore, there is no possibility that a fragment of the film covering the opening of the concave falls into the reagent. Therefore, it is possible to prevent contamination of the reagent through the film.

Further, the reagent open mechanism of the luminescence measurement system having such the features comprises a control section which outputs a drive signal to the triaxial actuator for moving the open needle in X-axis direction and/or Y-axis direction within an opening range of a concave in a state that the open needle is inserted into the film. According to such the configuration, it is possible to broaden the hole formed in the film. Such the configuration allows no contact between the film surface after being opened and the reagent dispensing nozzle. Accordingly, it is possible to prevent contamination of the reagent dispensing nozzle through the film surface.

Further, in the reagent open mechanism of the luminescence measurement system having such the features, the control section outputs a signal to the triaxial actuator for operation in Z-axis direction so that the tip end of the open needle is located between the film and an interface of the reagent filled in the reagent cartridge. Such the configuration allows no contact between the open needle and the reagent filled in the reagent cartridge. Therefore, there is no possibility to produce cross-contamination among reagents filled in concaves even in a case of plural concaves to be opened.

Further, in order to achieve the above objects, an open needle control method in a reagent open mechanism according to the present invention is an open needle control method in a luminescence measurement system which is capable of setting a reagent cartridge where a concave is filled with a reagent to be divided by a reagent dispensing nozzle and the opening of the concave is sealed by a film and which comprises: a triaxial actuator where horizontal movement axis is represented by X axis and Y axis and vertical movement axis is represented by Z axis; a reagent dispensing nozzle driven by the triaxial actuator; and an open needle driven by the triaxial actuator, comprising:

a first horizontal movement operation step of moving the open needle immediately above the concave to be opened;

a vertical movement operation step of lowering the open needle for forming a hole in the film; and a second horizontal movement operation step of moving thus lowered open needle in an X-axis direction and/or Y-axis direction for broadening the opening of the film.

Further, in such the open needle control method in the reagent open mechanism, in the vertical movement operation step, a tip end of the open needle is located between the film and an interface of the reagent filled in the concave. Such the control allows no contact between the open needle and the reagent filled in the reagent cartridge. Therefore, there is no possibility to produce cross-contamination between reagents filled in the concaves even in a case of plural concaves to be opened.

Further, in such the open needle control method in the reagent open mechanism, the second horizontal movement operation step is carried out within a range of the opening of the concave. Such the control allows no contact between the open needle and the reagent cartridge. Therefore, it is possible to prevent breakage of the package of the reagent cartridge which is caused by contact with the open needle and cross-contamination which is caused by splash of the reagent.

According to the reagent open mechanism of the luminescence measurement system having such the features, it is possible to prevent introduction of viable bacteria to an inside of the system due to contamination of the reagent and occurrence of contamination inside the system through the reagent.

Further, according to the open needle control method in the reagent open mechanism having such the features, similarly to effect of the above system, it is possible to prevent introduction of viable bacteria to an inside of the system due to contamination of the reagent and occurrence of contamination inside the system through the reagent.

BRIEF DESCRIPTION OF THE DRAWINGS

FIG. 3-A is a front block diagram showing a main configuration of a reagent open mechanism according to an embodiment.

FIG. 3-B is a plane block diagram showing a main configuration of the reagent open mechanism according to the embodiment.

FIG. 5-A is a plane view showing a configuration of a reagent/carrier container mount section.

FIG. 5-B is a plane view showing a reagent cartridge.

DETAILED DESCRIPTION OF THE EMBODIMENTS

Hereinafter, embodiments of the reagent open mechanism of the luminescence measurement system and the open needle control method in the reagent open mechanism according to the present invention are described with reference to the drawings.

The reagent open mechanism of the luminescence measurement system according to the present invention (hereinafter, simply referred to as reagent open mechanism 100, (ref. to FIGS. 3-A and 3-B)) is mounted on the luminescence measurement system (Biomaytector).

Figure 1:
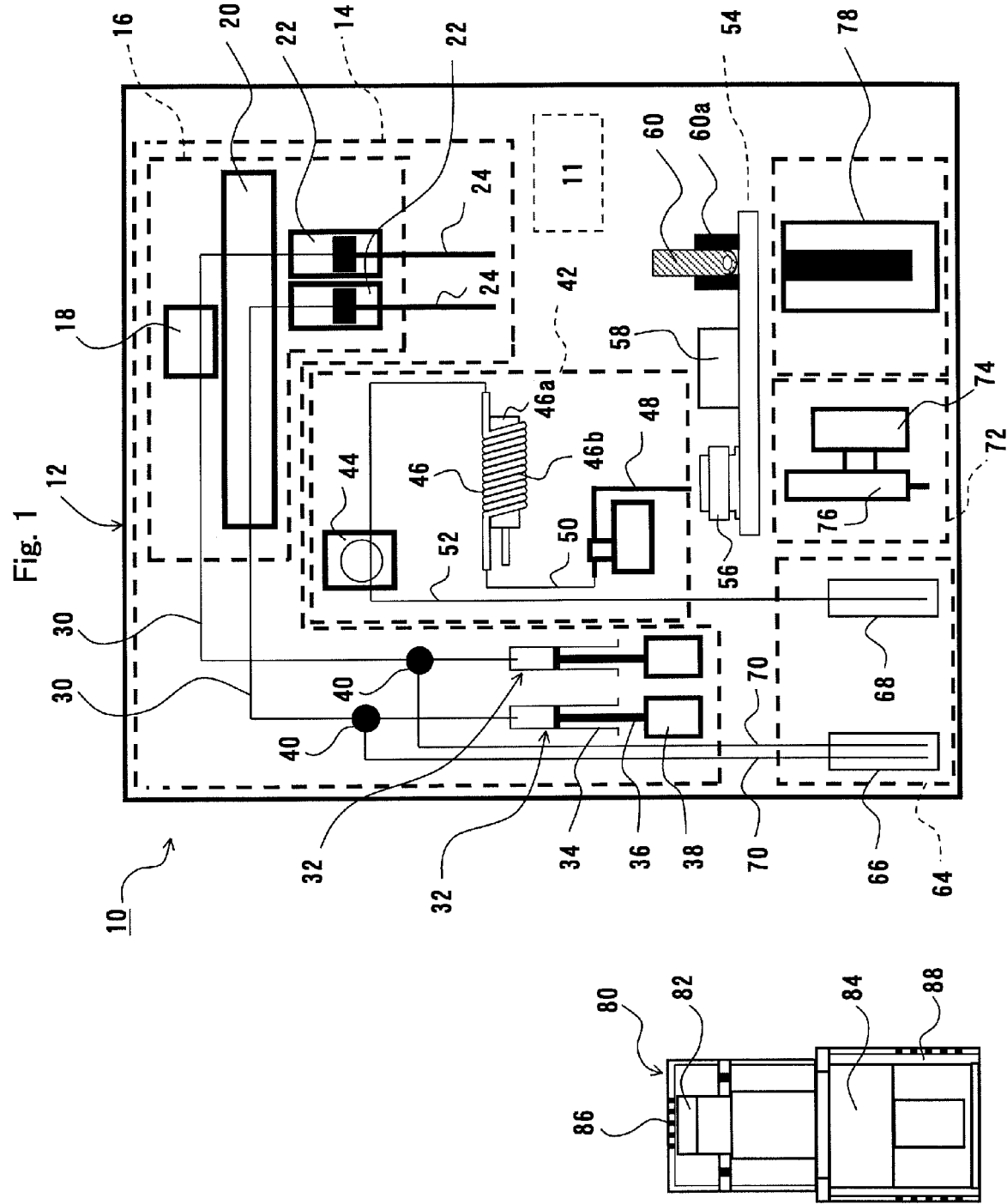
FIG. 1 is a block diagram showing a configuration of a luminescence measurement system.

First, an overall configuration of the luminescence measurement system (Biomaytector) 10 is described with reference to FIG. 1. FIG. 1 is a block diagram showing a configuration of the luminescence measurement system. This luminescence measurement system 10 is configured by a count unit 12 and a collection unit 80.

The count unit 12 has a reagent dispensing section 14, a hot water supply section 42, a reagent/carrier container mount section 54, a buffer supply section 64, a filtration section 72, a PMT (Photomultiplier tube) section 78, and an input/control section (control section) 11. Such the respective component elements are arranged in a casing.

Figure 2:
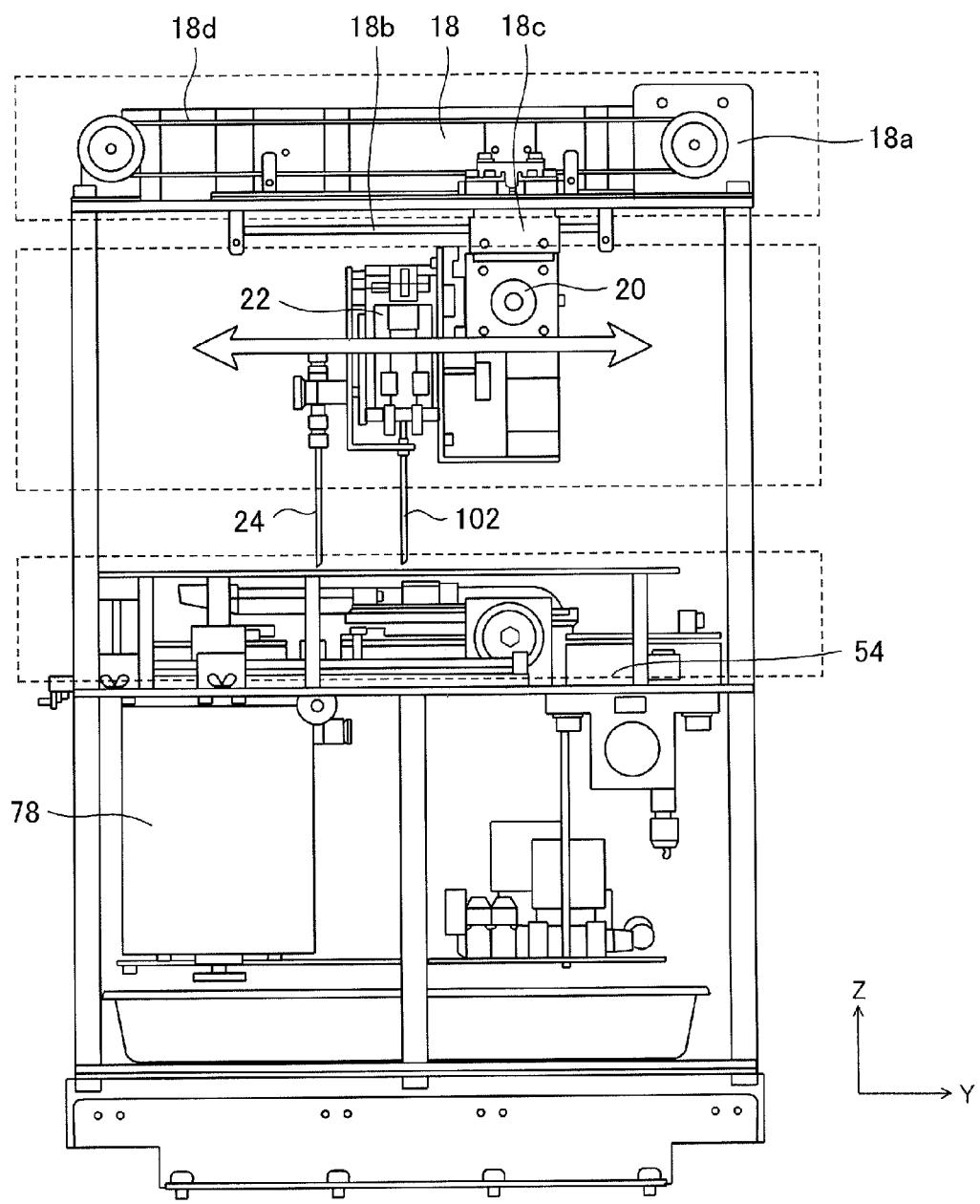
FIG. 2 is a schematic view showing a side configuration of a count unit.

The reagent dispensing section 14 is essentially configured by a triaxial actuator 16, a reagent dispensing nozzle 24, and a syringe pump 32. The triaxial actuator 16 is a means for moving the reagent dispensing nozzle 24 (described later in detail) to a desired location. FIG. 2 shows a side face of the count unit 12. As illustrated in FIG. 2, the triaxial actuator 16 is configured by a Y-axis mechanism section 18, an X-axis mechanism section 20, and a Z-axis mechanism section 22. The Y-axis mechanism section 18 is arranged at an upper part of the system, where space is not restricted so much. Therefore, in the count unit 12 according to the present embodiment, a stepping motor 18a is used as a driving actuator, and an operation section 18c attached to a linear guide 18b is slid by a driving belt 18d.

On the other hand, the X-axis mechanism section 20 and the Z-axis mechanism section 22 attached to the operation section 18*c* are difficult to have enough space. Therefore, a compact actuator is employed for both the X-axis mechanism section 20 and the Z-axis mechanism section 22. The compact actuator is a small-size actuator which integrates a motor and a projecting axis by incorporating a large-diameter thrust axis system into a hollow rotor. As an operation principle, the driving system is a stepping motor and the projecting axis is a ball screw. Accordingly, even such a compact size enables highly accurate positioning.

Figure 4:
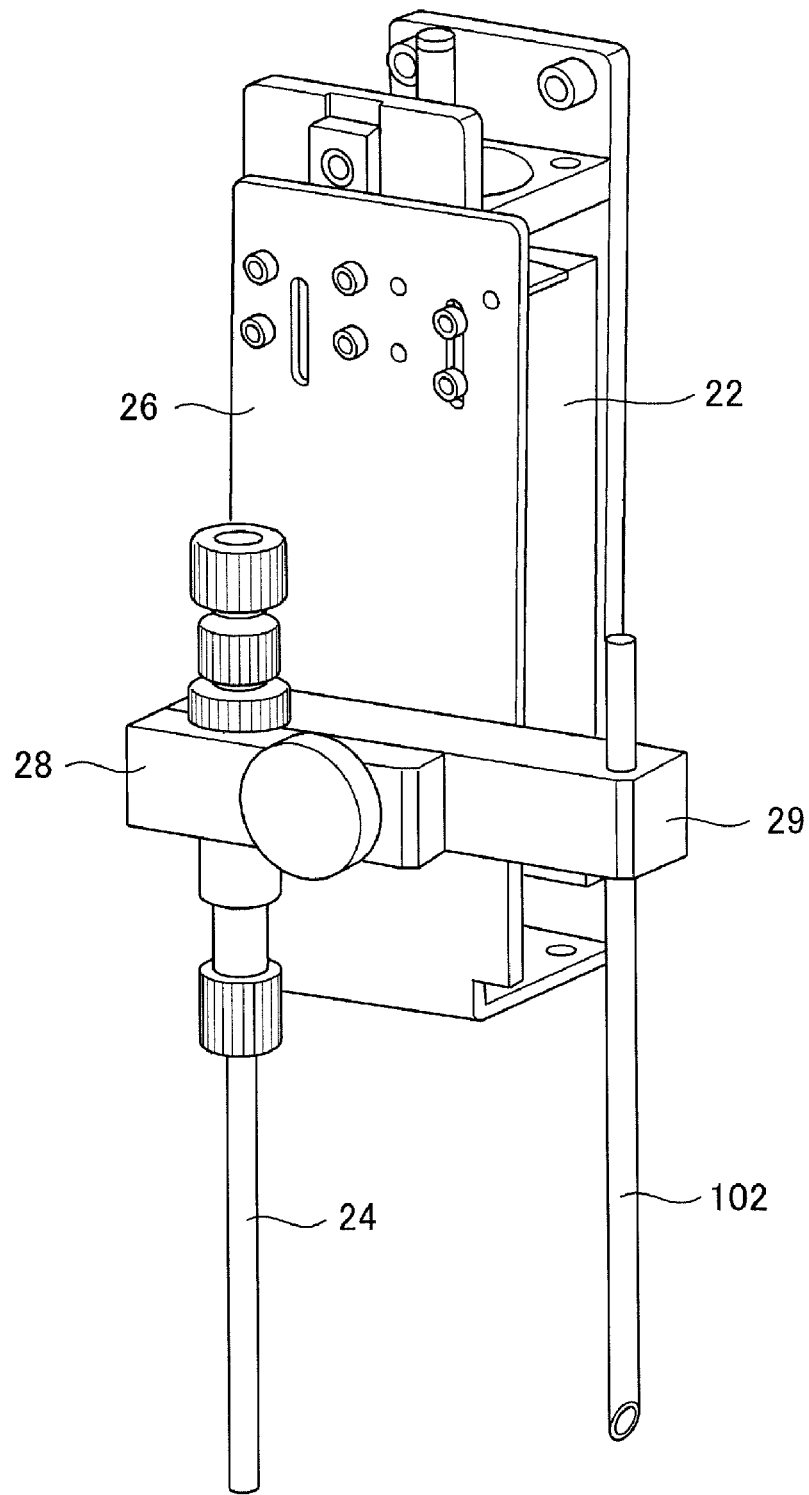
FIG. 4 is a perspective view showing relation between a Z-axis mechanism section and a fixation block, a reagent dispensing nozzle, and an open needle.

The reagent dispensing nozzle 24 is a nozzle which plays a role of dividing and dispensing various reagents used for luminescence counting. An attachment portion of the reagent dispensing nozzle 24 is shown in FIGS. 3 and 4. As shown in the figures, the reagent dispensing nozzle 24 is supported by a fixation block 28 equipped in a slide guide 26 attached to the compact actuator being the Z-axis mechanism section 22. Such the supporting configuration facilitates stabilization of an up-and-down operation. Here, FIG. 3-A is a front block diagram showing a relation between an overall configuration of the triaxial actuator 16 and the reagent dispensing nozzle 24. FIG. 3-B is a block diagram showing a plane configuration in FIG. 3-A. FIG. 4 is a perspective view showing a relation between the Z-axis mechanism section 22 and the reagent dispensing nozzle 24.

A dispensing operation pipe 30 connected to the syringe pump 32 described later in detail is connected to a back end of the reagent dispensing nozzle 24. The reagent dispensing nozzle 24 divides a reagent by applying negative pressure in this nozzle through the dispensing operation pipe 30 and dispends thus divided reagent by applying positive pressure in the nozzle. Here, the reagent dispensing nozzle 24 may be formed by a resin-made pipe, metal-made pipe as well as glass-made pipe.

The syringe pump 32 plays a role of controlling an actuation fluid (pure water according to the present embodiment) for dividing and dispensing reagent through the above-described reagent dispensing nozzle 24. The syringe pump 32 is essentially configured by a syringe 34, a plunger 36, and an actuator 38. The syringe 34 is a tank for storing pure water being an actuation fluid. The plunger 36 is a push stick which plays a role of introducing pure water into the syringe 34 and discharging pure water by applying negative pressure or positive pressure in the syringe 34. The actuator 38 is a driving means for plunging or extracting the plunger 36. It is possible to accurately control positioning by using a stepping motor and a ball screw for the actuator 38.

One end of the dispensing operation pipe 30 is connected to a tip end of the syringe 34 in the syringe pump 32 having such the configuration, and other end of the dispensing operation pipe 30 is connected to the reagent dispensing nozzle as described above. With thus connected dispensing operation pipe 30, pure water accumulates in the syringe 34 by extracting the plunger 36, negative pressure is applied inside the nozzle of the reagent dispensing nozzle 24, and a reagent is injected (divided) into the reagent dispensing nozzle 24. On the contrary, in a case of plunging the plunger 36, a pressure inside the reagent dispensing nozzle 24 increases because pure water discharged from the syringe 34 is moved to the reagent dispensing nozzle 24, and the reagent accumulated inside the reagent dispensing nozzle 24 is ejected (dispensed).

A buffer supply pipe 70 connected to a buffer supply section 64 described later in detail is connected to the dispensing operation pipe 30 through a distribution valve 40 such as three-way valve. According to such the configuration, it is possible to periodically change pure water being an operation fluid stored inside the dispensing operation pipe 30. Therefore, it is possible to prevent error of count data due to contamination of the operation fluid.

The hot water supply section 42 plays a role of supplying hot water for diluting the collection carrier. The hot water supply section 42 is essentially configured by a peristaltic pump 44, a heater 46, and a hot water supply nozzle 48. The peristaltic pump 44 is essentially configured by a resin tube, a roller, and an actuator (none of them shown in the figure). The resin tube is a tube used for sending solution, and transportation fluid (pure water in the present embodiment) flows therein. The tube which is mechanically compressed by the roller preferably has flexibility and durability and, for example, silicon tube is preferable. The roller consists of a rotation roller and plural revolution rollers revolving around the rotation roller. The roller plays a role of compressing the resin tube against a wall and squeezing by the revolution roller, and pushing out the transportation fluid which is closed in a compression region, in a direction of roller revolution. Force of reverting to the original form is applied on the resin tube thus compressed by the roller. Because the transportation fluid is an incompressible fluid, plural rollers are continuously revolved and then the transportation fluid is also continuously pushed out. Here, the actuator may be those capable of rotating plural rollers.

According to thus configured peristaltic pump 44, the pump itself is not contaminated since a contact portion with the transportation fluid (pure water in the present embodiment) is only inside the tube where the transportation fluid flows. Therefore, it is easy to maintain an aseptic condition and clean.

The heater 46 plays a role of heating the pure water being a transportation fluid. Although specific configuration of the heater 46 is not necessary, a cartridge heater and a tube heater are preferable in a case where compactness is emphasized. For example, in a case where the cartridge heater is employed, a heater body 46*a* is wound around by a pipe made of metal (hereinafter simply referred to as metal pipe 46*b*), and the pure water being a transportation fluid is sent through the metal pipe 46*b* thus wound as shown in FIG. 1. According to such the configuration, the pure water inside the metal pipe 46*b* is heated by heat transfer. Further, in a case where a tube heater is employed, the resin pipe (tube) and the like is wound around by a rubber heater, and the pure water being a transportation fluid sent through the resin tube is heated. According to such the configuration, a heat transfer rate becomes high by employing a silicon resin and the like for the resin tube. Further, since both of the resin tube and the rubber heater have flexibility, possibility of arrangement is high and it is possible to secure a heat region for long time. Therefore, it is possible to avoid temperature decrease, in other word, facilitate temperature stabilization. With respect to arrangement location of the heater 46, a fluid transportation distance after being heated is preferably short in order to avoid temperature decrease after being heated. Therefore, in the count unit 12 according to the present embodiment, the heater 46 is arranged between the above-described peristaltic pump 44 and the hot water supply nozzle 48 described later in detail.

The hot water supply nozzle 48 is an ejection nozzle for supplying hot water (pure water) which is transferred by the peristaltic pump 44 and heated by the heater 46 to a collection carrier cartridge 82 which is arranged in the reagent/carrier container mount section 54 described later in detail. It may be configured by a metal (SUS) pipe and the like or may be a glass pipe and a resin pipe as well. A hot water supply pipe 50 connected to the peristaltic pump 44 though the heater 46 is connected to an end on the other side of the ejection port in the hot water supply nozzle 48. Here, a suction side pipe 52 in the peristaltic pump 44 is connected to the buffer supply section 64 described later in detail.

According to the hot water supply section 42 having such the configuration, it is possible to continuously eject hot water from the hot water supply nozzle 48 by driving the peristaltic pump 44.

The reagent/carrier container mount section 54 is a stage for arranging a reagent used for the luminescence measurement and a collection carrier. A collection carrier cartridge holder 56, a reagent rack 58, a luminescence count tube holder 60a, and the like are arranged in the reagent/carrier container mount section 54.

The collection carrier cartridge holder 56 is a holder for setting the collection carrier cartridge 82. The collection carrier cartridge holder 56 is provided with a heat block having a heater so that thus set collection carrier cartridge 82 can be heated.

The reagent cartridge filled with a reagent used for the luminescence measurement is arranged in the reagent rack 58. As sown in FIG. 5-B, the reagent cartridge is a package where various types of reagents, pure water, and the like are filled in respective concaves which are separated into plural pieces (nine in an example shown in FIG. 5-B), and an upper opening of the concave is sealed with aluminum sheet (film) and the like. According to such the configuration, the reagent is not exposed to outside until the aluminum sheet is removed and opens, and stocked reagent is not contaminated by viable bacteria and the like. Here, FIG. 5-A is a top view of the reagent/carrier container mount section 54 and FIG. 5-B is a top view of the reagent cartridge 62.

A luminescence count tube 60 is arranged in the luminescence count tube holder 60a. The luminescence count tube 60 is a micro tube for conducting a luminescence reaction of ATP which is extracted from viable bacteria collected by the collection carrier cartridge 82.

The buffer supply section 64 has a reagent dispensing nozzle control water tank (hereafter simply referred to as control water tank 66) and a hot water supply water tank 68. Because a step of removing free ATP is not included in a step after the reagent dispensing nozzle 24 is used, a cleanliness level of the water (pure water) in the control water tank 66 filled in the dispensing operation pipe 30 which connects the syringe pump 32 and the reagent dispensing nozzle 24 is required to keep higher than that of the water (pure water) in the hot water supply water tank 68. Therefore, volume of the control water tank 66 is smaller than that of the hot water supply water tank 68 and accumulated water is appropriately exchanged. Here, water in the hot water supply water tank 68 requires larger volume than that of the control water tank 66, because it is poured in the collection carrier cartridge 82 set in the collection carrier cartridge holder 56.

The control water tank 66 thus set up is connected to the distribution valve 40 in the dispensing operation pipe 30 through the buffer supply pipe 70 so that pure water can be supplied to the dispensing operation pipe 30 by switching the distribution valve 40. Further, the hot water supply water tank 68 is connected to a suction side of the peristaltic pump 44 and suctioned by drive of the peristaltic pump 44.

The filtration section 72 plays a role of removing a collection carrier in the collection carrier cartridge 82 which is diluted by hot water ejected from the hot water supply nozzle 48. The filtration section 72 is essentially configured by a suction pump 74 and a suction head 76. The suction pump 74 is a pump for producing negative pressure inside the suction head 76 described later in detail. Further, the suction head 76 is a cylindrical body with a tip end opening.

Figure 6:
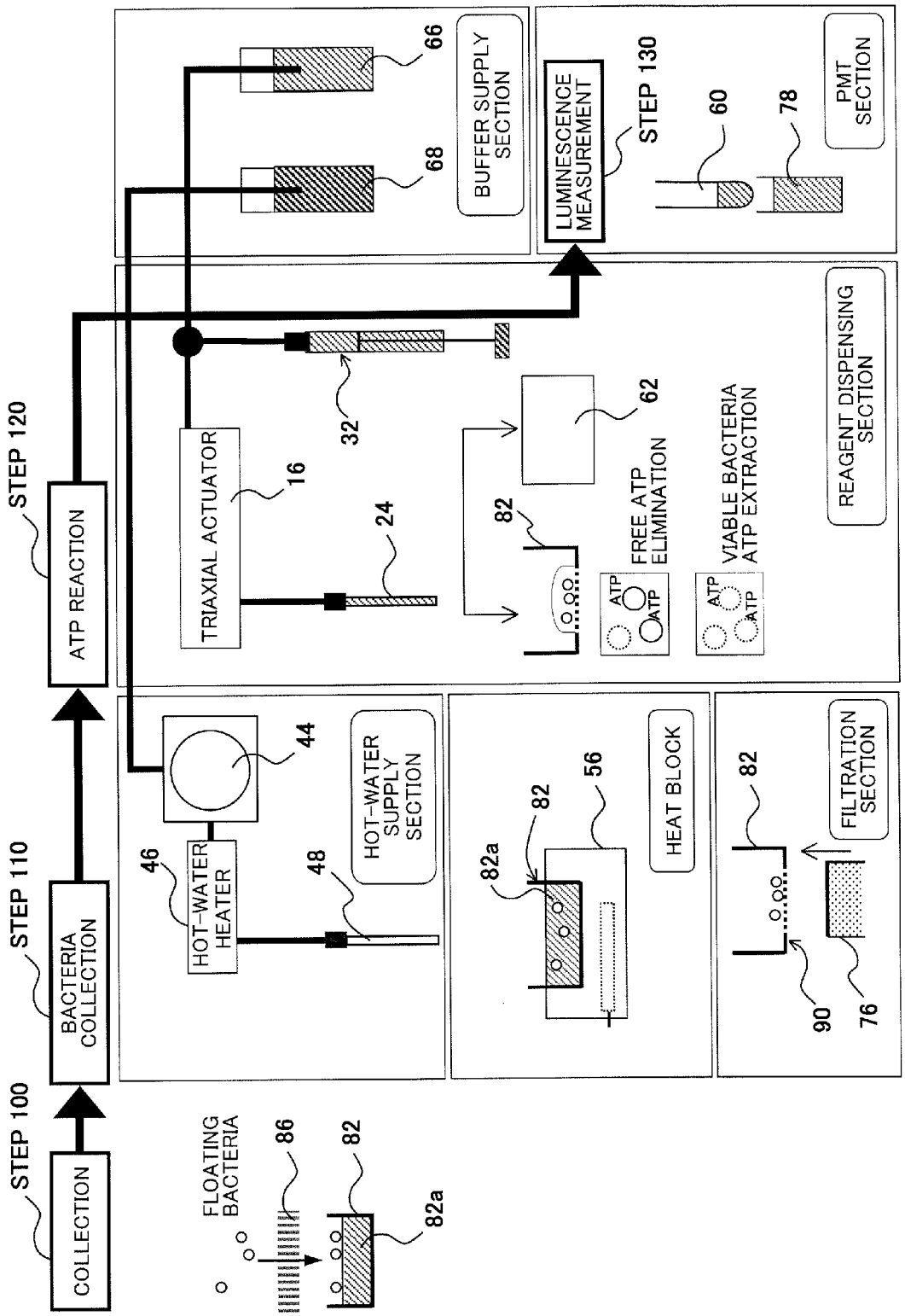
FIG. 6 is a flow diagram showing a state of luminescence measurement by the luminescence measurement system.

In the filtration section 72 having such essential configuration, a tip end is connected to a lower part of the collection carrier cartridge holder 56 and the suction pump 74 is driven so that the collection carrier diluted by hot water can be suctioned and removed trough a recovery filter 90 (Ref. to FIG. 6).

The PMT section 78 plays a role of measuring luminescence amount of the ATP in the luminescence count tube 60. In the count unit 12 according to the present embodiment, the PMT section 78 is a head-on type and arranged at lower part of the luminescence count tube 60 described above. According to such the configuration, light produced in the luminescence count tube 60 enters from the upper part of the PMT section 78 and luminescence amount is counted.

Here, the input/control section 11 which controls the above-described component elements with respect to an input value to the luminescence count system automates luminescence measurement.

The collection unit 80 shown on the left part of FIG. 1 is a system for collecting viable bacteria in the air into the collection carrier cartridge 82. The collection unit 80 is essentially configured by the collection carrier cartridge 82, a blower fan 84, an impactor nozzle head 86, and an exhaust filer 88.

The collection carrier cartridge 82 plays a role of collecting viable bacteria floating in the air. The collection carrier cartridge 82 is provided with a collection carrier 82a for collecting viable bacteria (Ref. to FIG. 6). The collection carrier 82a equipped in the collection carrier cartridge 82 according to the present embodiment is gelled at normal temperature and is solated by heating. Further, a cavity (not shown) to be filled with dilution hot water is equipped in a lower part of the collection carrier 82a. The recovery filter 90 (Ref. to FIG. 6) for filtering hot water which dilutes the collection carrier 82a is equipped in a lower part of the cavity.

The blower fan 84 plays a role of suctioning air into the collection unit 80 and striking floating bacteria in the air against the collection carrier 82a in the collection carrier cartridge 82. In order to prevent detection error due to contamination of the blower fan 84 itself, the blower fan 84 is preferably arranged in a downstream side from the collection carrier cartridge 82 (in a lower side in the collection unit 80 according to the present embodiment, because the suction port is located in an upper part). In the collection unit 80, it is possible to determine an amount of the collected air based on a blow amount and operation time of the blower fan 84.

The impactor nozzle head 86 is arranged in an upper part of the collection unit 80 and plays a role of a cover and accelerator of the collection carrier cartridge 82. A velocity of the air inflowing into the collection unit 80 is required high to some extent for striking viable bacteria against the collection carrier cartridge 82 and being supported. However, in order to obtain high velocity, there is a concern about size increase of the collection unit 80 because a size of the blower fan 84 and a rotation rate are required to increase.

Therefore, according to the present embodiment, in the impactor nozzle head 86, plural small-diameter openings are provided so that the air suctioned by the blower fan 84 passes through the small-diameter openings and strikes against the collection carrier 82a. In a case of constant air flow, it is possible to increase a velocity of passing fluid by narrowing an area of flow passage. Therefore, it is possible to obtain necessary velocity without increasing a size and a rotation rate of the blower fan 84.

The exhaust filter 88 is arranged in downstream side of the blower fan 84 (in a lower side in the collection unit 80 according to the present embodiment) and plays a role of removing dust included in the exhaust.

According to such the configuration, the collection unit 80 of the present embodiment can be made compact and light.

In the luminescence measurement system 10 consisting of the count unit 12 and the collection unit 80 having the above essential configuration, first, viable bacteria in the air are collected by the collection unit 80 (Step 10: Ref. to FIG. 6).

Next, the collection carrier cartridge 82 collecting viable bacteria is taken out from the collection unit 80 and set in the collection carrier cartridge holder 56 of the count unit 12. The collection carrier cartridge 82 thus set in the collection carrier cartridge holder 56 is heated by the heat block. The collection carrier is solated by heating. Thus solated collection carrier 82a is diluted by hot water supplied from the hot water supply nozzle 48. Thus diluted collection carrier 82a is suctioned and removed by the filtration section 72 through the recovery filter 90. Viable bacteria and free ATP thus collected by the collection carrier 82a remain in the recovery filter 90 (Step 110: Ref. to FIG. 6).

After filtering the collection carrier 82a, the reagent dispensing section 14 is operated for removing free ATP and dividing a viable bacteria sample. First, a reagent (for ATP removal) is divided from the reagent cartridge 62 by the reagent dispensing nozzle 24 and dispensed into the collection carrier cartridge 82, and free ATP is removed. By this operation, it is possible to prevent occurrence of count error of luminescence amount due to a luminescence reaction caused by the free ATP. Next, a reagent (for ATP extraction) is dispensed on the recovery filter 90 in the collection carrier cartridge 82 having been removed of the free ATP, and ATP is extracted from viable bacteria on the recovery filter 90 (Step 120: Ref. to FIG. 6).

An ATP extraction sample is divided from the recovery filter 90 in the collection carrier cartridge 82 and dispended into the luminescence count tube 60. A luminescence reagent is previously dispensed in the luminescence count tube 60, and a luminescence reaction simultaneously starts as ATP extraction sample is dispensed. In the luminescence reaction in the luminescence count tube 60, the luminescence strength is counted by the PMT section 78 (Step 130: Ref. to FIG. 6).

According to the luminescence measurement system 10 having such the essential configuration, because processes from a step of dividing the viable bacteria sample from the collection carrier cartridge 82 to a step of counting luminescence amount are automatically carried out inside the count unit 12 enclosed in an outer shell, there is a little possibility that a viable bacteria sample is affected by contamination. Further, because the luminescence reagent is previously dispensed into the luminescence count tube 60 set in the reagent/carrier container mount section 54 and subsequently the ATP extraction sample is dispensed, it is possible to count a self-background light of the reagent as well. Therefore, it is possible to accurately obtain a relation between luminescence amount and luminescence time and accurately perform calculation of an ATP amount based on a luminescence amount, in other words, count of viable bacteria number.

Next, a reagent open mechanism 100 according to the present embodiment is described. As shown in FIGS. 3-A and 3-B, the reagent open mechanism 100 is essentially configured by an open needle 102 and the above-described fixation block 28. The open needle 102 is retained by the fixation block 28, together with the above-described reagent dispensing nozzle 24 and driven by the triaxial actuator 16 (Ref. to FIG. 1). A material of the open needle 102 is not specifically limited, as long as the material has such strength that the needle can make a hole on the aluminum sheet (film) in the reagent cartridge 62. The open needle 102 according to the present embodiment is formed of metal rod-shape (cylinder-shape or pole-shape) material and a tip end is cut obliquely so that the needle has an acute portion and an obtuse portion at end face. According to such the configuration, the aluminum sheet is torn at the acute portion and pressed and bent at the obtuse portion without being torn (cut)). Therefore, there is no possibility that a fragment of the aluminum sheet covering the opening of concave does not fall on the reagent. Thus, it is possible to prevent contamination of the reagent through the aluminum sheet. Further, it is also possible to decrease a pressure required for an operation of making hole on the aluminum sheet.

The fixation block 28 fixes the reagent dispensing nozzle 24 and the open needle 102 in a location where the reagent dispensing nozzle 24 or the open needle 102 does not contact with component elements of the count unit 12 including the reagent cartridge 62 in the Z-axis operation during opening or dividing and dispensing the reagent. In other words, the fixation block 28 is extended to the Z-axis mechanism section 22 in a Y-axis direction, and the reagent dispensing nozzle 24 is attached to the tip end thereof in a Z-axis direction. An arm 29 extending in an X-direction is fixed to the fixation block 28 in a location which is displaced from an attachment location of the reagent dispensing nozzle 24 in the Y-axis direction. The open needle 102 extending in parallel with the reagent dispensing nozzle 24 in Z-axis direction is attached to a tip end of the arm 29. According to such the configuration, there is no possibility that the reagent dispensing nozzle 24 contacts with the reagent cartridge 62 when the open needle 102 makes a hole on the aluminum sheet. On the contrary, there is no possibility either that the open needle 102 contacts with the reagent cartridge 62 when the reagent dispensing nozzle 24 divides the reagent from the reagent cartridge 62.

The open needle 102 in such the retention state is configured so that the diameter of the open needle is larger (thicker) than that of the reagent dispensing nozzle 24. Inside the concave in the reagent cartridge 62 which is sealed by the aluminum sheet, cleanliness state is maintained until the aluminum sheet opens. However, a surface of the aluminum sheet which is exposed to outside is not necessarily clean. Therefore, a diameter of hole made on the aluminum sheet by the open needle 102 is larger than that of the reagent dispensing nozzle 24, so that the reagent dispensing nozzle 24 does not contact with the surface of the aluminum sheet during regent division. Accordingly, the reagent dispensing nozzle 24 is not contaminated due to the contact with the aluminum sheet. Here, the diameter of the open needle 102 is preferably twice or more larger than the diameter of reagent dispensing nozzle 24.

The triaxial actuator 16 having the open needle 102 and the reagent dispensing nozzle 24 drives by a drive signal from the input/control section 11 described above and moves the open needle 102 and the reagent dispensing nozzle 24. In the reagent open mechanism 100 according to the present embodiment, the input/control section 11 outputs a drive signal to the triaxial actuator 16 for slightly moving the open needle 102 in at least either of X-axis direction or Y-axis direction, after the open needle 102 moves in a Z-axis direction, in other words, after the open operation is completed. Here, a range of slight movement is within an area of the opening of concave which is formed on the reagent cartridge 62, so that the open needle 102 does not contact with a package of the reagent cartridge 62. According to such the operation, it is possible to broaden a hole of the aluminum sheet in the reagent cartridge 62. Therefore, it is possible to further reduce probability of contact between the reagent dispensing nozzle 24 and the aluminum sheet during the reagent division and reduce a risk that the reagent dispensing nozzle 24 is contaminated.

Further, the input/control section 11 according to the present embodiment outputs a drive signal during drive control in a Z-axis direction for the operation of opening the aluminum sheet so that a tip end of the open needle 102 is located between a surface of the aluminum sheet (a surface of the aluminum sheet before a hole is made) and an interface of a reagent filled in the concave of the reagent cartridge 62. According to such the configuration, the open needle 102 does not contact with the reagent filled in the concave. Therefore, there is no possibility that cross-contamination to each other occurs among the plural concaves which are filled with variety of reagents.

Figure 7:
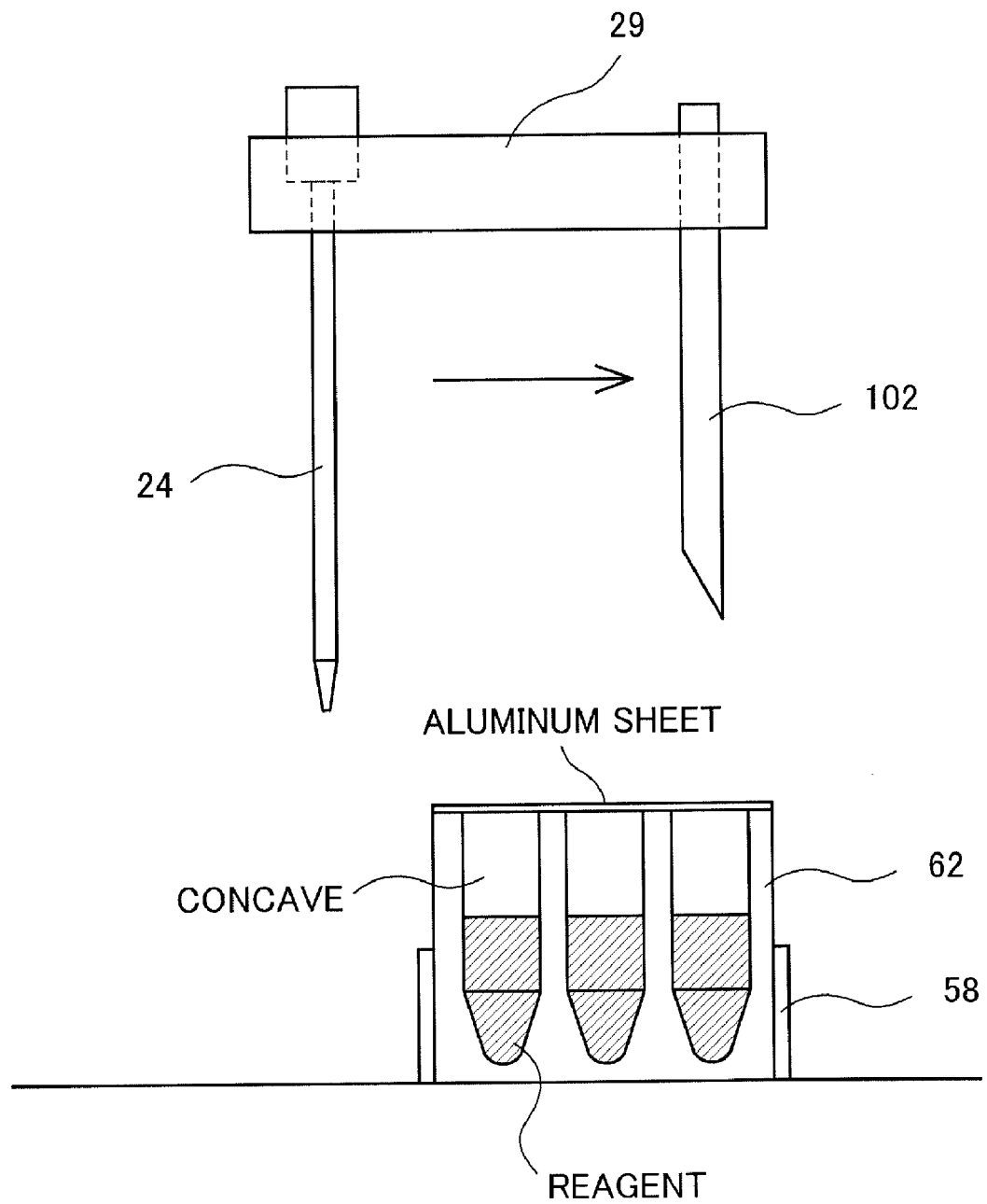
FIG. 7 is a view explaining a first horizontal movement operation among reagent open operations by the reagent open mechanism according to the embodiment.

In the reagent open mechanism 100 having such the configuration, first, the triaxial actuator 16 is driven by a drive signal from the input/control section 11 for moving the open needle 102 to immediately above the concave to be opened in the reagent cartridge 62 (the first horizontal movement operation: Ref. to FIG. 7).

Figure 8:
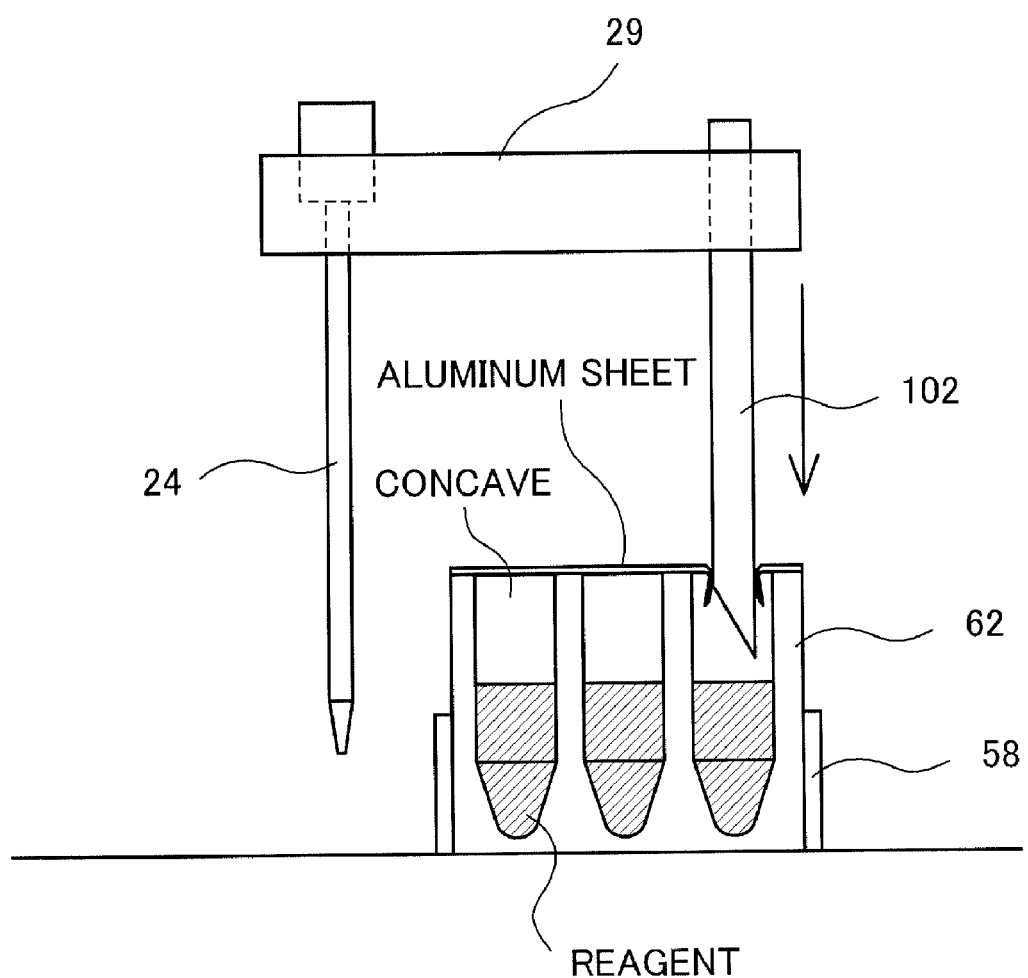
FIG. 8 is a view explaining a vertical movement operation among the reagent open operations by the reagent open mechanism according to the embodiment.

Next, the Z-axis mechanism section 22 in the triaxial actuator 16 is driven to cause the open needle 102 to vertically descend for making a hole on the aluminum sheet which seals the concave of the reagent cartridge 62. Here, the input/control section 11 outputs a drive signal to the Z-axis mechanism section 22 so that a tip end of the open needle 102 is located between the surface of aluminum sheet and the interface of reagent filled in the concave (vertical movement operation: Ref. to FIG. 8).

Figure 9:
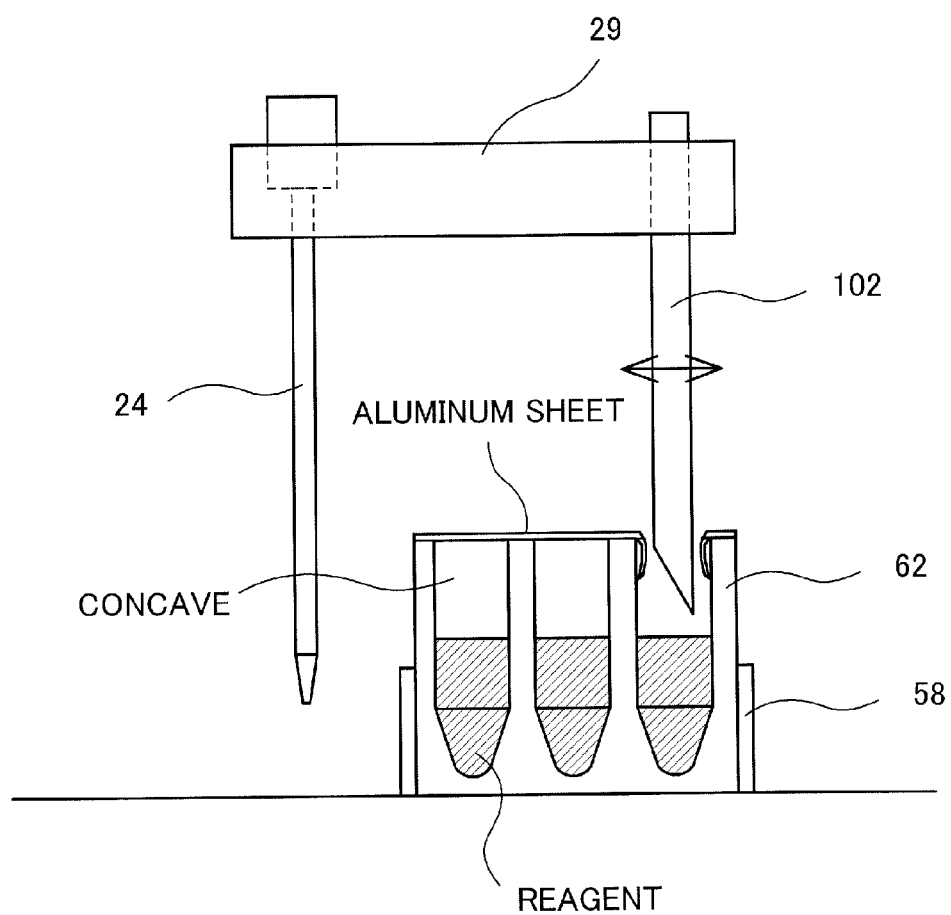
FIG. 9 is a view explaining a second horizontal movement operation among the reagent open operations by the reagent open mechanism according to the embodiment.

Next, the input/control section 11 outputs a drive signal to the X-axis mechanism section 20 and the Y-axis mechanism section 18 in the triaxial actuator 16 for slightly moving the open needle 102 in at least either of X-axis direction or Y-axis direction (the second horizontal movement operation: Ref. to FIG. 9).

Figure 10:
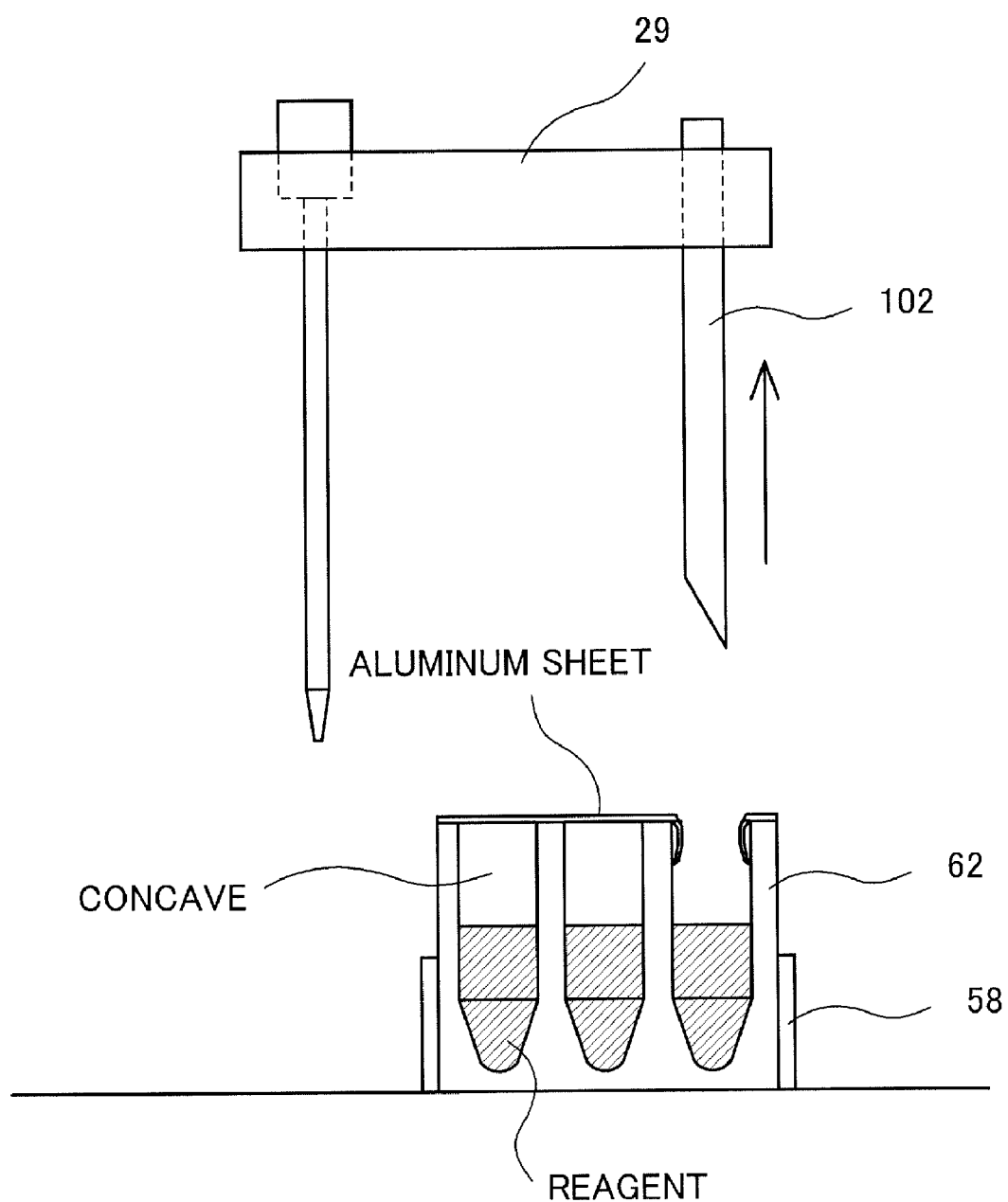
FIG. 10 is a view explaining an open needle retraction operation among the reagent open operations by the reagent open mechanism according to the embodiment.

Finally, a drive signal is outputted from the input/control section 11 to the Z-axis mechanism section 22 for raising the open needle 102, and the open needle 102 is pulled upward (Ref. to FIG. 10).

According to the reagent open mechanism 100 having such the configuration of the present embodiment, it is possible to open the reagent cartridge 62 in a state that the reagent cartridge 62 is being set in the reagent rack 58. Therefore, the reagent cartridge 62 is opened inside the count unit 12 and it is possible to prevent contamination of the reagent. Accordingly, it is possible to prevent introduction of viable bacteria to an inside of the system due to contamination of the reagent and prevent contamination occurrence inside the system through the reagent.

Further, since the triaxial actuator 16 for driving the reagent dispensing nozzle 24 is used as the drive mechanism of the open needle 102, there is no need to include an actuator for driving only the open needle 102 and it is possible to make the system compact.

REFERENCE NUMERALS

10 Luminescence system (BIOMAYTECTOR)
11 Input/control section
12 Count unit
14 Reagent dispensing section
16 Triaxial actuator
18 Y-axis mechanism section
20 X-axis mechanism section
22 Z-axis mechanism section
24 Reagent dispensing nozzle
26 Slide guide
28 Fixation block
30 Dispensing operation pipe
32 Syringe pump
34 Syringe
36 Plunger
38 Actuator
40 Distribution valve
42 Hot water supply section
44 Peristaltic pump
46 Heater
48 Hot water supply nozzle
50 Hot water supply pipe
52 Suction side pipe
54 Reagent/carrier container mount section
56 Collection carrier cartridge holder
58 Reagent rack
60 Luminescence count tube
62 Reagent cartridge
64 Buffer supply section
66 Control water tank
68 Hot water supply water tank
70 Buffer supply pipe
72 Filtration section
74 Suction pump
76 Suction head
78 PMT section
80 Collection unit
82 Collection carrier cartridge
84 Blower fan
86 Impactor nozzle head
88 Exhaust filter
90 Recovery filter
100 Reagent open mechanism
102 Open needle

The invention claimed is:

1. A reagent open mechanism of a luminescence measurement system which is capable of setting a reagent cartridge where a reagent is filled in a concave and an opening of the concave is sealed by a film, comprising:
   a triaxial actuator configured for horizontal movement represented by X axis and Y axis and vertical movement is represented by Z axis;
   a reagent dispensing nozzle operably connected to and driven by the triaxial actuator and capable of withdrawing a reagent from the reagent cartridge;
   a needle operably connected to and driven by the triaxial actuator and configured to open a hole in the film;
   a fixation block to which the reagent dispensing nozzle and the needle are operably connected, the fixation block being configured to arrange the reagent dispensing nozzle and the needle in such a location that the reagent dispensing nozzle or the needle does not contact with component elements of the luminescence measurement system including the reagent cartridge in the Z-axis operation during film opening time or reagent dividing and dispensing time; and
   a control section configured to output a drive signal to the triaxial actuator for moving the needle in an X-axis direction and/or a Y-axis direction within an opening range of the concave in a state in which the needle is inserted into the film.

2. The reagent open mechanism of the luminescence measurement system according to claim 1, wherein a diameter of the needle is larger than that of the reagent dispensing nozzle.

3. The reagent open mechanism of the luminescence measurement system according to claim 1, wherein the needle is a cylinder with an obliquely-cut tip end, and end faces have a portion acute with a side face and a portion obtuse to a side face.

4. The reagent open mechanism of the luminescence measurement system according to claim 1, wherein the control section is configured to output a signal to the triaxial actuator for operation in a Z-axis direction so that a tip end of the needle is located between the film and an interface of the reagent filled in the reagent cartridge.

5. The reagent open mechanism of the luminescence measurement system according to claim 1, wherein the reagent dispensing nozzle is operably connected to the triaxial actuator by the fixation block.

6. The reagent open mechanism of the luminescence measurement system according to claim 1, further comprising an arm connected to the fixation block, wherein the needle is connected to the arm.

* * * * *